United States Patent
Rubin et al.

(10) Patent No.: US 11,844,769 B2
(45) Date of Patent: Dec. 19, 2023

(54) USE OF CYSTEAMINE AND DERIVATIVES THEREOF TO SUPPRESS TUMOR METASTASES

(71) Applicants: MESHABERASE, LLC, Potomac, MD (US); The united States of America, as Represented by the Secretary, Department of Health and Human Services, Bethesda, MD (US)

(72) Inventors: Benjamin Rubin, Potomac, MD (US); Mark Gilbert, Bethesda, MD (US); Jinkyu Jung, Bethesda, MD (US)

(73) Assignees: MESHABERASE, LLC, Potomac, MD (US); The United States of America, as Represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 17/337,095

(22) Filed: Jun. 2, 2021

(65) Prior Publication Data
US 2021/0290569 A1 Sep. 23, 2021

Related U.S. Application Data

(63) Continuation of application No. 16/594,827, filed on Oct. 7, 2019, now Pat. No. 11,052,057, which is a continuation of application No. 16/244,427, filed on Jan. 10, 2019, now abandoned, which is a continuation of application No. 15/699,745, filed on Sep. 8, 2017, now abandoned, which is a continuation of application No. 15/065,355, filed on Mar. 9, 2016, now abandoned, which is a continuation of application No. 14/256,687, filed on Apr. 18, 2014, now abandoned.

(60) Provisional application No. 61/814,010, filed on Apr. 19, 2013.

(51) Int. Cl.
| | |
|---|---|
| A61K 31/145 | (2006.01) |
| A61K 45/06 | (2006.01) |
| A61K 9/00 | (2006.01) |
| A61K 9/28 | (2006.01) |
| A61K 9/48 | (2006.01) |

(52) U.S. Cl.
CPC .......... A61K 31/145 (2013.01); A61K 9/0053 (2013.01); A61K 9/28 (2013.01); A61K 9/4891 (2013.01); A61K 45/06 (2013.01)

(58) Field of Classification Search
CPC .................................................. A61K 31/145
See application file for complete search history.

(56) References Cited

U.S. PATENT DOCUMENTS

| | | | |
|---|---|---|---|
| 7,652,070 | B2 | 1/2010 | Rubin |
| 2005/0245433 | A1 | 3/2005 | Chan et al. |
| 2009/0048154 | A1 | 2/2009 | Chan et al. |
| 2009/0076166 | A1 | 3/2009 | Dohil et al. |
| 2011/0070272 | A1 | 3/2011 | Chan et al. |
| 2012/0302940 | A1 | 11/2012 | Ray |

FOREIGN PATENT DOCUMENTS

| | | |
|---|---|---|
| CN | 101797242 A | 8/2010 |
| WO | 2007079670 A1 | 7/2007 |
| WO | 2007089670 A2 | 8/2007 |
| WO | 2009070781 A1 | 6/2009 |

OTHER PUBLICATIONS

Jeitner et al. cancer letters, 1996, 103, 85-90. (Year: 1996).*
Qiu, et al., "Cystamine ameliorates liver fibrosis induced by carbon tetrachloride via inhibition of tissue transglutaminase." World J. Gastroenterol., 13(32), 4328-4332, Aug. 28, 2007. (Year: 2007).
Anderson, et al., "Combination Therapy Including a Gelatinase Inhibitor and Cytotoxic Agent Reduces Local Invasion and Metastasis of Murine Lewis Lung Carcinoma." Cancer Res., 56:715-8 (1996).
Apffel, et al., "Tumor rejection in experimental animals treated with radioprotective thiols." Cancer Res., 35:429-37 (1975).
Basset, et al., "Matrix metalloproteinases as stromal effectors of human carcinoma progression: therapeutic implications." Matrix Biol., 15:535-41 (1997).
Besouw, et al., "Pharmacokinetics of cysteamine in a cystinosis patient treated with hemodialysis." Pediatr. Nephrol., 26:639-40 (2011).
Bramhall, "Stromal degradation by the malignant epithelium in pancreatic cancer and the therapeutic potential of proteolytic inhibition." J. Hepatobiliary Pancreat. Surg., 5:392-401 (1998).
Chang, et al., "The many faces of metalloproteases: cell growth, invasion, angiogenesis and metastasis." Trends Cell Biol., 11:S37-43 (2001).
D'Angelo, et al., "Authentic matrix vesicles contain active metalloproteases (MMP). a role for matrix vesicle-associated MMP-13 in activation of transforming growth factor-beta." J. Biol. Chem., 276:11347-53 (2001).
De Ferreyra, et al., "Therapeutic effectiveness of cystamine and cysteine to reduce liver cell necrosis induced by several hepatotoxins." Toxicol. Appl. Pharmacol., 48(2):221-8 (1979).
Dohil, et al., "Long-term treatment of cystinosis in children with twice daily cysteamine." J. Pediatr., 156:823-7 (2010).
Dohil, et al., "The evaluation and treatment of gastrointestinal disease in children with cystinosis receivinq cvsteamine." J. Pediatr., 143:224-30 (2003).
Dohil, et al., "Understanding intestinal cysteamine bitartrate absorption." J. Pediatr., 148:764-9 (2006).

(Continued)

*Primary Examiner* — Genevieve S Alley
(74) *Attorney, Agent, or Firm* — Mendelsohn Dunleavy, P.C.

(57) ABSTRACT

The present Disclosure is directed to methods for inhibiting or suppressing metastasis of a tumor in a mammalian subject using a cysteamine product, e.g., cysteamine or cystamine or a derivative thereof. Also described herein is a method for treating pancreatic cancer in a mammalian subject by administering a cysteamine product described herein.

13 Claims, 1 Drawing Sheet

(56) References Cited

OTHER PUBLICATIONS

Eccles, et al., "Control of lymphatic and hematogenous metastasis of a rat mammary carcinoma by the matrix metalloproteinase inhibitor batimastat (BB-94)." Cancer Res., 56:2815-22 (1996).
Fujisawa, et al., "A novel role of interleukin-13 receptor alpha2 in pancreatic cancer invasion and metastasis." Cancer Res., 69:8678-85 (2009).
Gahl, et al., "Cystinosis." N. Engl. J. Med., 347(2):111-21 (2002).
Jeitner, et al., "Inhibition of the proliferation of human neural neoplastic cell lines by cysteamine." Cancer Lett., 103:85-90 (1996).
Jeitner, et al., "Possible oncostatic action of cysteamine on the pituitary glands of oestrogen-primed hyperprolactinaemic rats." J. Endocrinol., 127:119-27 (1990).
Jonas, et al., "Plasma cysteamine concentrations in children treated for cystinosis." J. Pediatr., 100:321-3 (1982).
Kilian, et al., "Matrix metalloproteinase inhibitor RO 28-2653 decreases liver metastasis by reduction of MMP-2 and MMP-9 concentration in BOP-induced ductal pancreatic cancer in Syrian Hamsters: inhibition of matrix metalloproteinases in pancreatic cancer." Prostaglandins Leukot. Essent. Fatty Acids, 75:429-34 (2006).
Kleta, et al., "Pharmacological treatment of nephropathic cystinosis with cysteamine." Expert Opin. Pharmacother., 5:2255-62 (2004).
Markello, et al., "Improved renal function in children with cystinosis treated with cysteamine." N. Engl. J. Med., 328:1157-62 (1993).
Nakashima, et al., "Interleukin-13 receptor alpha2 DNA prime boost vaccine induces tumor immunity in murine tumor models." J. Transl. Med., 8:116 (2010).
Prescott, et al., "Cysteamine or N-acetylcysteine for paracetamol poisoning?" Br. Med. J., 1(6116):856-7 (1978).
Prescott, et al., "Haemodialysis in paracetomol self-poisoning." Lancet 2(7778):652 (1972).
Schmalfeldt, et al., "Increased expression of matrix metalloproteinases (MMP)-2, MMP-9, and the urokinase-type plasminogen activator is associated with progression from benign to advanced ovarian cancer." Clin. Cancer Res., 7:2396-404 (2001).
Shimamura, et al., Interleukin 13 mediates signal transduction through interleukin 13 receptor alpha2 in pancreatic ductal adenocarcinoma: role of IL-13 Pseudomonas exotoxin in pancreatic cancer therapy. Clin. Cancer Res., 16:577-86 (2010).
Shinoda, et al., "A novel matrix metalloproteinase inhibitor, FYK-1388 suppresses tumor growth, metastasis and angiogenesis by human fibrosarcoma cell line." Int. J. Oncol., 22:281-8 (2003).
Smolin, et al., "A comparison of the effectiveness of cysteamine and phosphocysteamine in elevating plasma cysteamine concentration and decreasing leukocyte free cystine in nephropathic cystinosis." Pediatr. Res., 23:616-20 (1988).
Sparano, et al., Randomized phase III trial of marimastat versus placebo in patients with metastatic breast cancer who have responding or stable disease after first-line chemotherapy: Eastern Cooperative Oncology Group trial E2196, J. Clin. Oncol., 22:4683-90 (2004).
Steward, "Marimastat (BB2516): current status of development." Cancer Chemother. Pharmacol., 43(Suppl):S56-60 (1999).
Tamahashi, et al., "Expression and intracellular localization of matrix metalloproteinases in intraductal papillary mucinous neoplasms of the pancreas." Virchows Arch., 453:79-87 (2008).
Tatsuta, et al., "Inhibitory effect of prolonged administration of cysteamine on experimental carcinogenesis in rat stomach induced by N-methyl-N'-nitro-N-nitrosoguanidine." Int. J. Cancer, 41:423-6 (1988).
Unak, et al., "Gold nanoparticle probes: design and in vitro applications in cancer cell culture." Colloids Surf B. Biointerfaces, 90:217-26 (2012).
Wang, et al., "Solanum nigrum Linn. water extract inhibits metastasis in mouse melanoma cells in vitro and in vivo." J. Agric. Food Chem., 58:11913-23 (2010).
Watanabe, et al., "The effects of ranitidine and cysteamine on intestinal metaplasia induced by X-irradiation in rats." Acta. Pathol. Jpn., 38:1285-96 (1988).
Wenner, et al., "The effects of cysteamine on the upper gastrointestinal tract of children with cystinosis." Pediatr. Nephrol., 11:600-3 (1997).
Wu, et al., "New strategy of efficient inhibition of cancer cells by carborane carboxylic acid-CdTe nanocomposites." Nanomedicine, 8(6):860-9 (2011).
Yamada, et al., "The killing effect of 4-S-cysteaminylphenol, a newly synthesized melanin precursor on B16 melanoma cell lines." Br. J. Cancer, 63:187-90 (1991).
Brown, "Ongoing trials with matrix metallopreoteinase inhibitors." Expert Opin. Investig. Drugs, 9:2167-77 (2000). (Year: 2000).
Cystagon(R) (cysteamine bitartrate)-Package Insert. Mylan Pharmaceutical Inc. (2007). (Year: 2007).
Fujisawa, et al., "Targeting IL-13R2 in human pancreatic ductal adenocarcinoma with combination therapy of IL-13-PE and gemcitabine." International J. Cancer, 128:1221-3 (2011) (Year: 2011).
Gangoiti, et al., "Pharmacokinetics of enteric-coated cystamine bitartrate in healthy adults: a pilot study." Br. J. Clin. Pharmacol. 70:376-82 (2010). (Year: 2010).
Mitchell, et al., Acetaminophen-induced hepatic injury: protective role of glutathione in man and rationale for therapy. Clin. Pharmacol. Ther., 16(4):676-84 (1974). (Year: 1974).
Mollenhauer, et al., "Distribution of extracellular matrix proteins in pancreatic ductal adenocarcinoma and its influence on tumor cell proliferation in vitro." Pancreas, 2:14-24 (1987). (Year: 1987).
Wan, "Autophagy-mediated chemosensitization by cysteamine in cancer cells." Internal. J. Can., 129:1087-95 (2011). (Year: 2011).

* cited by examiner

USE OF CYSTEAMINE AND DERIVATIVES THEREOF TO SUPPRESS TUMOR METASTASES

CROSS REFERENCE TO RELATED APPLICATIONS

This application is a continuation of U.S. application Ser. No. 16/594,827 filed on Oct. 7, 2019 (allowed), which is a continuation of U.S. application Ser. No. 16/244,427 filed on Jan. 10, 2019 (abandoned), which is a continuation of U.S. application Ser. No. 15/699,745 filed on Sep. 8, 2017 (abandoned), which is a continuation of U.S. application Ser. No. 15/065,355 filed on Mar. 9, 2016 (abandoned), which is a continuation of U.S. application Ser. No. 14/256,687 filed on Apr. 18, 2014 (abandoned), which claims the priority benefit of U.S. Provisional Patent Application No. 61/814,010, filed Apr. 19, 2013, the disclosures of each of which are incorporated by reference herein in their entireties.

STATEMENT OF GOVERNMENT INTEREST

This invention was funded by the National Institutes of Health of the United States of America. The government has certain rights in this invention.

FIELD OF THE INVENTION

The present invention relates to the use of cysteamine or cystamine or derivatives thereof to treat, inhibit or suppress metastasis of a tumor. The present invention also related to the use of cysteamine or cystamine or derivatives thereof to treat pancreatic cancer.

BACKGROUND

Cysteamine ($HS-CH_2-CH_2-NH_2$) is a small sulfhydryl compound that is able to cross cell membranes easily due to its small size. Cysteamine plays a role in formation of the protein glutathione (GSH) precursor, and is currently FDA approved for use in the treatment of cystinosis, an intra-lysosomal cystine storage disorder. In cystinosis, cysteamine acts by converting cystine to cysteine and cysteine-cysteamine mixed disulfide, which are then both able to leave the lysosome through the cysteine and lysine transporters respectively (Gahl et al., N Engl J Med 2002; 347(2):111-21). Within the cytosol the mixed disulfide can be reduced by its reaction with glutathione and the cysteine released can be used for further GSH synthesis. Treatment with cysteamine has been shown to result in lowering of intracellular cystine levels in circulating leukocytes (Dohil et al., J. Pediatr 148(6):764-9, 2006).

Cysteamine is also discussed in (Prescott et al., Lancet 1972; 2(7778):652; Prescott et al., Br Med J 1978; 1(6116): 856-7; Mitchell et al., Clin Pharmacol Ther 1974; 16(4): 676-84; Toxicol Appl Pharmacol. 1979 48(2):221-8; Qiu et al., World J Gastroenterol. 13:4328-32, 2007. Unfortunately, the sustained concentrations of cysteamine necessary for therapeutic effect are difficult to maintain due to rapid metabolism and clearance of cysteamine from the body, with nearly all administered cysteamine converted to taurine in a matter of hours. These difficulties are transferred to patients in the form of high dosing levels and frequencies, with all of the consequent unpleasant side effects associated with cysteamine (e.g., gastrointestinal distress and body odor) See the package insert for CYSTAGON® (cysteamine bitartrate). International Publication No. WO 2007/079670 discloses enterically coated cysteamine products and a method of reducing dosing frequency of cysteamine.

Cysteamine is addressed in International Patent Application Nos. WO 2009/070781, and WO 2007/089670, and U.S. Patent Publication Nos. 20110070272, 20090048154, and 20050245433.

In the cancer field, studies have reported anti-cancer effects of cysteamine with respect to cancer development and proliferation. Cysteamine prevented the development of metaplasia and carcinogenesis of mammary tumor and gastric cancers induced chemically and by radiation (6-8). Cysteamine by itself or conjugated with nanoparticles or other compounds suppress cancer cell proliferation derived from neural neoplastic tumors (9), SMIVIC-7721 hepatocellular carcinoma (10), breast cancer (11), and melanoma cell lines (12) in vitro.

SUMMARY

In one aspect, described herein is a method of inhibiting or suppressing metastasis of a tumor in a mammalian subject comprising administering cysteamine, cystamine or pharmaceutically acceptable salts thereof to the subject in an amount effective to inhibit metastasis of the tumor.

In another aspect, described herein is a method of treating pancreatic cancer in a mammalian subject comprising administering cysteamine, cystamine or pharmaceutically acceptable salts thereof to the subject in an amount effective to treat the cancer.

In various embodiments, the cysteamine, cystamine or pharmaceutically acceptable salts thereof is administered orally, optionally being formulated for delayed release. In some embodiments, the cysteamine, cystamine or pharmaceutically acceptable salt thereof is formulated in a enterically coated tablet or capsule.

The delayed release formulation, in some embodiments, comprises an enteric coating that releases the cysteamine or cystamine when the formulation reaches the small intestine or a region of the gastrointestinal tract of a subject in which the pH is greater than about pH 4.5.

In some embodiments, the cysteamine, cystamine or pharmaceutically acceptable salts thereof is administered less than four times a day (e.g., three times, two times or once a day). In some embodiments, the cysteamine, cystamine or pharmaceutically acceptable salts thereof is administered twice a day.

In various embodiments of the disclosure, the cysteamine, cystamine or pharmaceutically acceptable salt thereof is administered in a dose of about of 0.01 mg to 1000 mg per kg (mg/kg) of body weight per day. In some embodiments, the cysteamine, cystamine or pharmaceutically acceptable salt thereof is administered at a daily dose ranging from about 10 mg/kg to about 250 mg/kg, or from about 100 mg/kg to about 250 mg/kg, or from about 60 mg/kg to about 100 mg/kg or from about 50 mg/kg to about 90 mg/kg, or from about 30 mg/kg to about 80 mg/kg, or from about 20 mg/kg to about 60 mg/kg, or from about 10 mg/kg to about 50 mg/kg. Further, the effective dose may be 0.5 mg/kg, 1 mg/kg, 5 mg/kg, 10 mg/kg, 15 mg/kg, 20 mg/kg/25 mg/kg, 30 mg/kg, 35 mg/kg, 40 mg/kg, 45 mg/kg, 50 mg/kg, 55 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, 250 mg/kg, 300 mg/kg, 350 mg/kg, 400 mg/kg, 450 mg/kg, 500 mg/kg, and may increase by 25 mg/kg increments up to 1000 mg/kg, or may range between any two of the foregoing values. In some embodiments, the cysteamine product is administered at a total daily dose of from approximately 0.25 g/m² to 4.0 g/m² body surface area, about 0.5-2.0 g/m² body surface area, or 1-1.5 g/m² body surface area, or 1-1.95 g/m² body surface area, or 0.5-1 g/m² body surface area, or about 0.7-0.8 g/m² body surface area, or about 1.35 g/m² body surface area, or about 1.3 to about 1.95 grams/m²/day, or about 0.5 to about 1.5 grams/m2/day, or about 0.5 to about 1.0 grams/m²/day, e.g., at least about 0.3, 0.4, 0.5, 0.6, 0.7, 0.8, 0.9, 1.0, 1.1, 1.2, 1.3, 1.4, 1.5, 1.6, 1.7, 1.8, 1.9 or 2 g/m², or up to about 0.8, 0.9, 1.0, 1.1, 1.2, 1.3, 1.4, 1.5, 1.6, 1.7, 1.8, 1.9, 2.0, 2.2, 2.5, 2.7, 3.0, 3.25, 3.5 or 3.75 g/m² or may range between any two of the foregoing values.

In some embodiments, the administering results in increased thiol levels compared to levels before administration of the cysteamine, cystamine or pharmaceutically acceptable salts thereof.

In some embodiments, the administering modulates enzymatic activity of a matrix metalloproteinase (MMP, e.g., MMP-1, MMP-2, MMP-3, MMP-4, MMP-5, MMP-6, MMP-6, MMP-8, MMP-9, MMP-10, MMP-11, MMP-12, MMP-13 and/or MMP-14.) in a cancer cell of the tumor. In some embodiments, enzymatic activity of MMP is decreased in a primary tumor.

In some embodiments, the administering decreases metastatic nodules and/or ascites in the subject.

The methods described herein are useful for the inhibition or suppression of metastasis of any cancer. In some embodiments, the cancer is selected from the group consisting of breast cancer, melanoma, prostate cancer, pancreatic cancer, head and neck cancer, lung cancer, non small-cell lung carcinoma, renal cancer, colorectal cancer, colon cancer, ovarian cancer, liver cancer and gastric cancer.

Aspects of the invention that are described herein as methods (especially methods that involve treatment) can alternatively be described as (medical) uses of cysteamine, cystamine or pharmaceutically salts thereof. For example, in one variation, described herein the use of cysteamine, cystamine or pharmaceutically acceptable salts thereof to inhibit or suppress metastasis of a tumor. In another variation, described herein is the use of cysteamine, cystamine or pharmaceutically acceptable salts thereof to treat pancreatic cancer.

The agents and compositions described herein for use in treatment are themselves aspects of the invention also, e.g., as compositions of matter.

In the treatment methods (or uses) described herein, the methods optionally comprise administering an adjunct cancer therapy to the subject in combination with the cysteamine, cystamine or pharmaceutically acceptable salts thereof. In some embodiments, the adjunct cancer therapy is selected from the group consisting of chemotherapy, surgery, radiotherapy, cancer vaccines, immunotherapy, gene therapy, thermotherapy and laser therapy.

In some embodiments, the methods (or uses) described herein further comprise administering a further therapeutic agent selected from the group consisting of an MMP inhibitor, a chemotherapeutic agent, a growth inhibitory agent and a cytokine.

With respect to any combination treatments described herein, the cysteamine, cystamine or pharmaceutically acceptable salts thereof can be administered simultaneously with the other active agents, which may be in admixture with the agent or may be in a separate composition. Each composition preferably includes a pharmaceutically acceptable diluent, adjuvant, or carrier. When the agents are separately administered, they may be administered in any order.

In another aspect, described herein is a method of decreasing matrix metalloproteinase (MMP) enzymatic activity in a cancer cell comprising contacting the cell with cysteamine, cystamine or pharmaceutically acceptable salts thereof in an amount effective to decrease MMP enzymatic activity in the cancer cell. In various embodiments, the MMP is selected from the group consisting of MMP-1, MMP-2, MMP-3, MMP-4, MMP-5, MMP-6, MMP-6, MMP-8, MMP-9, MMP-10, MMP-11, MMP-12, MMP-13 and MMP-14. In various embodiments, the MMP is selected from the group consisting of MMP-9, MMP-12 and MMP-14. In various embodiments, the MMP is MMP-9.

The foregoing summary is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document.

In addition to the foregoing, the invention includes, as an additional aspect, all embodiments of the invention narrower in scope in any way than the variations defined by specific paragraphs above. For example, certain aspects of the invention that are described as a genus, and it should be understood that every member of a genus is, individually, an aspect of the invention. Also, aspects described as a genus or selecting a member of a genus, should be understood to embrace combinations of two or more members of the genus. Although the applicant(s) invented the full scope of the invention described herein, the applicants do not intend to paragraph subject matter described in the prior art work of others. Therefore, in the event that statutory prior art within the scope of a paragraph is brought to the attention of the applicant(s) by a Patent Office or other entity or individual, the applicant(s) reserve the right to exercise amendment rights under applicable patent laws to redefine the subject matter of such a paragraph to specifically exclude such statutory prior art or obvious variations of statutory prior art from the scope of such a paragraph. Variations of the invention defined by such amended paragraphs also are intended as aspects of the invention.

DETAILED DESCRIPTION

The present disclosure relates, in general, to the discovery of the anti-invasive and/or anti-metastatic effects of cysteamine in human cancers.

Definitions

As used herein and in the appended claims, the singular forms "a," "and," and "the" include plural referents unless the context clearly dictates otherwise. Thus, for example, reference to "a derivative" includes a plurality of such derivatives and reference to "a patient" includes reference to one or more patients and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and products, the exemplary methods, devices and materials are described herein.

The documents discussed above and throughout the text are provided solely for their disclosure prior to the filing date of the present application. Nothing herein is to be construed as an admission that the inventors are not entitled to antedate such disclosure by virtue of prior disclosure. Each document is incorporated by reference in its entirety with particular attention to the disclosure for which it is cited.

The following references provide one of skill with a general definition of many of the terms used in this disclosure: Singleton, et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger, et al. (eds.), Springer Verlag (1991); and Hale and Marham, THE HARPER COLLINS DICTIONARY OF BIOLOGY (1991).

As used herein, a "therapeutically effective amount" or "effective amount" refers to that amount of a cysteamine product, e.g., cysteamine, cystamine or a pharmaceutically acceptable salt thereof, sufficient to result in amelioration of symptoms, for example, treatment, healing, prevention or amelioration of the relevant medical condition, or an increase in rate of treatment, healing, prevention or amelioration of such conditions, typically providing a statistically significant improvement in the treated patient population. When referencing an individual active ingredient, administered alone, a therapeutically effective dose refers to that ingredient alone. When referring to a combination, a therapeutically effective dose refers to combined amounts of the active ingredients that result in the therapeutic effect, whether administered in combination, including serially or simultaneously. In various embodiments, a therapeutically effective amount of the cysteamine product ameliorates symptoms associated with various cancers, including but not limited to, loss of appetite, oral pain, upper abdominal pain, fatigue, abdominal swelling, persistent aches, bone pain, nausea, vomiting, constipation, weight loss, headaches, rectal bleeding, night sweats, digestive discomfort, and painful urination.

"Treatment" refers to prophylactic treatment or therapeutic treatment. In certain embodiments, "treatment" refers to administration of a compound or composition to a subject for therapeutic or prophylactic purposes.

A "therapeutic" treatment is a treatment administered to a subject who exhibits signs or symptoms of pathology for the purpose of diminishing or eliminating those signs or symptoms. The signs or symptoms may be biochemical, cellular, histological, functional or physical, subjective or objective.

A "prophylactic" treatment is a treatment administered to a subject who does not exhibit signs of a disease or exhibits only early signs of the disease, for the purpose of decreasing the risk of developing pathology. The compounds or compositions of the disclosure may be given as a prophylactic treatment to reduce the likelihood of developing a pathology or to minimize the severity of the pathology, if developed.

"Diagnostic" means identifying the presence, extent and/or nature of a pathologic condition. Diagnostic methods differ in their specificity and selectivity. While a particular diagnostic method may not provide a definitive diagnosis of a condition, it suffices if the method provides a positive indication that aids in diagnosis.

"Pharmaceutical composition" refers to a composition suitable for pharmaceutical use in a subject animal, including humans and mammals. A pharmaceutical composition comprises a therapeutically effective amount of a cysteamine product, optionally another biologically active agent, and optionally a pharmaceutically acceptable excipient, carrier or diluent. In an embodiment, a pharmaceutical composition encompasses a composition comprising the active ingredient(s), and the inert ingredient(s) that make up the carrier, as well as any product that results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the disclosure and a pharmaceutically acceptable excipient, carrier or diluent.

"Pharmaceutically acceptable carrier" refers to any of the standard pharmaceutical carriers, buffers, and the like, such as a phosphate buffered saline solution, 5% aqueous solution of dextrose, and emulsions (e.g., an oil/water or water/oil emulsion). Non-limiting examples of excipients include adjuvants, binders, fillers, diluents, disintegrants, emulsifying agents, wetting agents, lubricants, glidants, sweetening agents, flavoring agents, and coloring agents. Suitable pharmaceutical carriers, excipients and diluents are described in Remington's Pharmaceutical Sciences, 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, intravenous or intraperitoneal injection; or topical, transdermal, or transmucosal administration).

A "pharmaceutically acceptable salt" is a salt that can be formulated into a compound for pharmaceutical use, including but not limited to metal salts (e.g., sodium, potassium, magnesium, calcium, etc.) and salts of ammonia or organic amines Examples of cysteamine derivatives include hydrochloride, bitartrate and phosphocysteamine derivatives. Cystamine and cystamine derivatives include sulfated cystamine.

As used herein "pharmaceutically acceptable" or "pharmacologically acceptable" salt, ester or other derivative of an active agent comprise, for example, salts, esters or other derivatives refers to a material that is not biologically or otherwise undesirable, i.e., the material may be administered to an individual without causing any undesirable biological effects or without interacting in a deleterious manner with any of the components of the composition in which it is contained or with any components present on or in the body of the individual.

As used herein, the term "unit dosage form" refers to physically discrete units suitable as unitary dosages for human and animal subjects, each unit containing a predetermined quantity of a compound of the disclosure calculated in an amount sufficient to produce the desired effect, optionally in association with a pharmaceutically acceptable excipient, diluent, carrier or vehicle. The specifications for the novel unit dosage forms of the present disclosure depend on the particular compound employed and the effect to be achieved, and the pharmacodynamics associated with each compound in the host.

As used herein, the term "subject" encompasses mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. The term does not denote a particular age or gender. In various embodiments the subject is human Cancer The invention is contemplated to be useful with respect to any cancer type. Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor. In some embodiments, the tumor is associated with a cancer selected from the group consisting of breast cancer, melanoma, prostate cancer, pancreatic cancer, head and neck cancer, lung cancer, non small-cell lung carcinoma, renal cancer, colorectal cancer, colon cancer, ovarian cancer, liver cancer and gastric cancer. In some embodiments, the cancer is pancreatic cancer.

Matrix Metalloproteinases (MMPs)

In some embodiments, the cysteamine product inhibits enzymatic activity of one or more matrix metalloproteinases (MMPs) in a cancer cell selected from the group consisting of MMP-1, MMP-2, MMP-3, MMP-4, MMP-5, MMP-6, MMP-7, MMP-8, MMP-9, MMP-10, MMP-11, MMP-12, MMP-13 and MMP-14. In some embodiments, the cysteamine product inhibits the enzymatic activity of MMP-2, MMP-9, MMP-12 and/or MMP-14 in a cancer cell. MMPs are a group of zinc-dependent endopeptidases implicated in mammalian angiogenesis, wound healing, and tissue remodeling (17). In cancer, MMPs play an important role in cell invasion and metastasis by controlling degradation of the extracellular matrix (18). In particular, MMP-9 plays a central role in pancreatic cancer invasion, and its inhibition decreases liver metastasis of pancreatic cancer (15,19). Hence, many MMP inhibitors of broad to narrow specificity have been investigated for their anti-cancer effects. Some MMP inhibitors successfully suppress tumor growth and metastasis in animal models (20-22), but they fail to show anti-cancer effects in clinical settings.

Cysteamine/Cystamine

Cysteamine plays a role in formation of the protein glutathione (GSH) precursor. In cystinosis, cysteamine acts by converting cystine to cysteine and cysteine-cysteamine mixed disulfide which are then both able to leave the lysosome through the cysteine and lysine transporters respectively (Gahl et al., N Engl J Med 2002; 347(2):111-21). Within the cytosol the mixed disulfide can be reduced by its reaction with glutathione and the cysteine released can be used for further GSH synthesis. The synthesis of GSH from cysteine is catalyzed by two enzymes, gamma-glutamylcysteine synthetase and GSH synthetase. This pathway occurs in almost all cell types, with the liver being the major producer and exporter of GSH. The reduced cysteine-cysteamine mixed disulfide will also release cysteamine, which, in theory is then able to re-enter the lysosome, bind more cystine and repeat the process (Dohil et al., J Pediatr 2006; 148(6):764-9). In a recent study in children with cystinosis, enteral administration of cysteamine resulted in increased plasma cysteamine levels, which subsequently caused prolonged efficacy in the lowering of leukocyte cystine levels (Dohil et al., J Pediatr 2006; 148(6):764-9). This may have been due to "re-cycling" of cysteamine when adequate amounts of drug reached the lysosome. If cysteamine acts in this fashion, then GSH production may also be significantly enhanced.

Cysteamine is a potent gastric acid-secretagogue that has been used in laboratory animals to induce duodenal ulceration; studies in humans and animals have shown that cysteamine-induced gastric acid hypersecretion is most likely mediated through hypergastrinemia. Cysteamine is currently FDA approved for use in the treatment of cystinosis, an intra-lysosomal cystine storage disorder. In previous studies performed in children with cystinosis who suffered regular upper gastrointestinal symptoms, a single oral dose of cysteamine (11-23 mg/kg) was shown to cause hypergastrinemia and a 2 to 3-fold rise in gastric acid-hypersecretion, and a 50% rise in serum gastrin levels. Symptoms suffered by these individuals included abdominal pain, heartburn, nausea, vomiting, and anorexia. U.S. patent application Ser. No. 11/990,869 and published International Publication No. WO 2007/089670 (each of which is incorporated by reference herein in its entirety) showed that cysteamine induced hypergastrinemia arises, in part, as a local effect on the gastric antral-predominant G-cells in susceptible individuals. The data also suggest that this is also a systemic effect of gastrin release by cysteamine Depending on the route of administration, plasma gastrin levels usually peak after intragastric delivery within 30 minutes whereas the plasma cysteamine levels peak later.

Subjects with cystinosis are required to ingest oral cysteamine (CYSTAGON®) every 6 hours day and night. When taken regularly, cysteamine can deplete intracellular cystine by up to 90% (as measured in circulating white blood cells), and this had been shown to reduce the rate of progression to kidney failure/transplantation and also to obviate the need for thyroid replacement therapy. Because of the difficulty in taking CYSTAGON®, reducing the required dosing improves the adherence to therapeutic regimen. International Publication No. WO 2007/089670 demonstrates that delivery of cysteamine to the small intestine reduces gastric distress and ulceration and increases AUC. Delivery of cysteamine into the small intestine is useful due to improved absorption rates from the small intestine, and/or less cysteamine undergoing hepatic first pass elimination when absorbed through the small intestine. A decrease in leukocyte cystine was observed within an hour of treatment.

In addition, sulfhydryl (SH) compounds such as cysteamine, cystamine, and glutathione are active intracellular antioxidants. Cysteamine protects animals against bone marrow and gastrointestinal radiation syndromes. The rationale for the important anti-oxidant properties of SH compounds is further supported by observations in mitotic cells. These are the most sensitive to radiation injury in terms of cell reproductive death and are noted to have the lowest level of SH compounds. Conversely, S-phase cells, which are the most resistant to radiation injury using the same criteria, have demonstrated the highest levels of inherent SH compounds. In addition, when mitotic cells were treated with cysteamine, they became very resistant to radiation. It has also been noted that cysteamine may directly protect cells against induced mutations. The protection is thought to result from scavenging of free radicals, either directly or via release of protein-bound GSH. An enzyme that liberates cysteamine from coenzyme A has been reported in avian liver and hog kidney. Recently, studies have reported a protective effect of cysteamine against the hepatotoxic agents acetaminophen, bromobenzene, and phalloidine.

Cystamine, in addition to its role as a radioprotectant, has been found to alleviate tremors and prolong life in mice with the gene mutation for Huntington's disease (HD). The drug may work by increasing the activity of proteins that protect nerve cells, or neurons, from degeneration. Cystamine appears to inactivate an enzyme called transglutaminase and thus results in a reduction of huntingtin protein (Nature Medicine (2002) 8, 143-149). In addition, cystamine was found to increase the levels of certain neuroprotective proteins. However, due to the current methods and formulation of delivery of cystamine, degradation and poor uptake require excessive dosing.

Cysteamine Products

In another aspect, the disclosure provides cysteamine products for use in the methods described herein.

A "cysteamine product" in the present disclosure refers generally to cysteamine, cystamine, or a biologically active metabolite or derivative thereof, or combination of cysteamine and cystamine, and includes cysteamine or cystamine salts, esters, amides, alkylate compounds, prodrugs, analogs, phosphorylated compounds, sulfated compounds, nitrosylated and glycosylated compounds or other chemically modified forms thereof (e.g., chemically modified forms prepared by labeling with radionucleotides or enzymes and chemically modified forms prepared by attachment of polymers such as polyethylene glycol). Thus, the cysteamine or cystamine can be administered in the form of a pharmacologically acceptable salt, ester, amide, prodrug or analog or as a combination thereof. In various embodiments, the cysteamine product includes cysteamine, cystamine or derivatives thereof. In any of the embodiments described herein, a cysteamine product may optionally exclude N-acetylcysteine.

Salts, esters, amides, prodrugs and analogs of the active agents may be prepared using standard procedures known to those skilled in the art of synthetic organic chemistry and described, for example, by J. March, "Advanced Organic Chemistry: Reactions, Mechanisms and Structure," 4th Ed. (New York: Wiley-Interscience, 1992). For example, basic addition salts are prepared from the neutral drug using conventional means, involving reaction of one or more of the active agent's free hydroxyl groups with a suitable base. Generally, the neutral form of the drug is dissolved in a polar organic solvent such as methanol or ethanol and the base is added thereto. The resulting salt either precipitates or may be brought out of solution by addition of a less polar solvent. Suitable bases for forming basic addition salts include, but are not limited to, inorganic bases such as sodium hydroxide, potassium hydroxide, ammonium hydroxide, calcium hydroxide, trimethylamine, or the like. Preparation of esters involves functionalization of hydroxyl groups which may be present within the molecular structure of the drug. The esters are typically acyl-substituted derivatives of free alcohol groups, i.e., moieties which are derived from carboxylic acids of the formula R—COOH where R is alkyl, and typically is lower alkyl. Esters can be reconverted to the free acids, if desired, by using conventional hydrogenolysis or hydrolysis procedures. Preparation of amides and prodrugs can be carried out in an analogous manner Other derivatives and analogs of the active agents may be prepared using standard techniques known to those skilled in the art of synthetic organic chemistry, or may be deduced by reference to the pertinent literature.

In various embodiments, the cysteamine product does not refer to nanoparticles (including, but not limited to, gold, silver, cadmium and iron nanoparticles) comprising cysteamine (e.g., Wu et al., Nanomedicine: Nanotechnology, Biology and Medicine, 8:860, 869, 2011; Ghosh et al., Biomaterials, 34:807-816, 2013; Unak et al., Surf. N. Niointerfaces, 90:217-226, 2012; Petkova et al, Nanoscale Res. Lett., 7:287, 2012; and U.S. Patent Publication No. 2010/0034735 or cysteamine incorporated into another active agent (e.g., Fridkin et al., J. Comb. Chem., 7:977-986, 2005).

Pharmaceutical Formulations

The disclosure provides cysteamine products useful in the treatment of cancer (e.g., to inhibit or suppress metastasis of a tumor or the treatment of pancreatic cancer). To administer cysteamine products to patients or test animals, it is preferable to formulate the cysteamine products in a composition comprising one or more pharmaceutically acceptable carriers. Pharmaceutically or pharmacologically acceptable carriers or vehicles refer to molecular entities and compositions that do not produce allergic, or other adverse reactions when administered using routes well-known in the art, as described below, or are approved by the U.S. Food and Drug Administration or a counterpart foreign regulatory authority as an acceptable additive to orally or parenterally administered pharmaceuticals. Pharmaceutically acceptable carriers include any and all clinically useful solvents, dispersion media, coatings, antibacterial and antifungal agents, isotonic and absorption delaying agents and the like.

Pharmaceutical carriers include pharmaceutically acceptable salts, particularly where a basic or acidic group is present in a compound. For example, when an acidic substituent, such as —COOH, is present, the ammonium, sodium, potassium, calcium and the like salts, are contemplated for administration. Additionally, where an acid group is present, pharmaceutically acceptable esters of the compound (e.g., methyl, tert-butyl, pivaloyloxymethyl, succinyl, and the like) are contemplated as preferred forms of the compounds, such esters being known in the art for modifying solubility and/or hydrolysis characteristics for use as sustained release or prodrug formulations.

When a basic group (such as amino or a basic heteroaryl radical, such as pyridyl) is present, then an acidic salt, such as hydrochloride, hydrobromide, acetate, maleate, pamoate, phosphate, methanesulfonate, p-toluenesulfonate, and the like, is contemplated as a form for administration.

In addition, compounds may form solvates with water or common organic solvents. Such solvates are contemplated as well.

The cysteamine products may be administered orally, parenterally, transocularly, intranasally, transdermally, transmucosally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramusclar, intramammary, intraperitoneal, intrathecal, retrobulbar, intrapulmonary injection and or surgical implantation at a particular site is contemplated as well. Generally, compositions for administration by any of the above methods are essentially free of pyrogens, as well as other impurities that could be harmful to the recipient. Further, compositions for administration parenterally are sterile.

Pharmaceutical compositions of the disclosure containing a cysteamine product as an active ingredient may contain pharmaceutically acceptable carriers or additives depending on the route of administration. Examples of such carriers or additives include water, a pharmaceutically acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof, as appropriate, depending on the dosage form of the disclosure.

Formulation of the pharmaceutical composition will vary according to the route of administration selected (e.g., solution, emulsion). An appropriate composition comprising the cysteamine product to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers.

A variety of aqueous carriers, e.g., water, buffered water, 0.4% saline, 0.3% glycine, or aqueous suspensions may contain the active compound in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

In some embodiments, the cysteamine product disclosed herein can be lyophilized for storage and reconstituted in a suitable carrier prior to use. Any suitable lyophilization and reconstitution techniques can be employed. It is appreciated by those skilled in the art that lyophilization and reconstitution can lead to varying degrees of activity loss and that use levels may have to be adjusted to compensate.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

In one embodiment, the disclosure provides use of an enterically coated cysteamine product composition. Enteric coatings prolong release until the cysteamine product reaches the intestinal tract, typically the small intestine. Because of the enteric coatings, delivery to the small intestine is improved thereby improving uptake of the active ingredient while reducing gastric side effects. Exemplary enterically coated cysteamine products are described in International Publication No. WO 2007/089670.

In some embodiments, the coating material is selected such that the therapeutically active agent is released when the dosage form reaches the small intestine or a region in which the pH is greater than pH 4.5. The coating may be a pH-sensitive materials, which remain intact in the lower pH environs of the stomach, but which disintegrate or dissolve at the pH commonly found in the small intestine of the patient. For example, the enteric coating material begins to dissolve in an aqueous solution at pH between about 4.5 to about 5.5. For example, pH-sensitive materials will not undergo significant dissolution until the dosage form has emptied from the stomach. The pH of the small intestine gradually increases from about 4.5 to about 6.5 in the duodenal bulb to about 7.2 in the distal portions of the small intestine. In order to provide predictable dissolution corresponding to the small intestine transit time of about 3 hours (e.g., 2-3 hours) and permit reproducible release therein, the coating should begin to dissolve at the pH range within the small intestine. Therefore, the amount of enteric polymer coating should be sufficient to substantially dissolved during the approximate three hour transit time within the small intestine, such as the proximal and mid-intestine.

Enteric coatings have been used for many years to arrest the release of the drug from orally ingestible dosage forms. Depending upon the composition and/or thickness, the enteric coatings are resistant to stomach acid for required periods of time before they begin to disintegrate and permit release of the drug in the lower stomach or upper part of the small intestines. Examples of some enteric coatings are disclosed in U.S. Pat. No. 5,225,202 which is incorporated by reference fully herein. As set forth in U.S. Pat. No. 5,225,202, some examples of coating previously employed are beeswax and glyceryl monostearate; beeswax, shellac and cellulose; and cetyl alcohol, mastic and shellac, as well as shellac and stearic acid (U.S. Pat. No. 2,809,918); polyvinyl acetate and ethyl cellulose (U.S. Pat. No. 3,835,221); and neutral copolymer of polymethacrylic acid esters (Eudragit L30D) (F. W. Goodhart et al., Pharm. Tech., pp. 64-71, April 1984); copolymers of methacrylic acid and methacrylic acid methylester (Eudragits), or a neutral copolymer of polymethacrylic acid esters containing metallic stearates (Mehta et al., U.S. Pat. Nos. 4,728,512 and 4,794,001). Such coatings comprise mixtures of fats and fatty acids, shellac and shellac derivatives and the cellulose acid phthlates, e.g., those having a free carboxyl content. See, Remington's at page 1590, and Zeitova et al. (U.S. Pat. No. 4,432,966), for descriptions of suitable enteric coating compositions. Accordingly, increased adsorption in the small intestine due to enteric coatings of cysteamine product compositions can result in improved efficacy.

Generally, the enteric coating comprises a polymeric material that prevents cysteamine product release in the low pH environment of the stomach but that ionizes at a slightly higher pH, typically a pH of 4 or 5, and thus dissolves sufficiently in the small intestines to gradually release the active agent therein. Accordingly, among the most effective enteric coating materials are polyacids having a pKa in the range of about 3 to 5. Suitable enteric coating materials include, but are not limited to, polymerized gelatin, shellac, methacrylic acid copolymer type CNF, cellulose butyrate phthalate, cellulose hydrogen phthalate, cellulose proprionate phthalate, polyvinyl acetate phthalate (PVAP), cellulose acetate phthalate (CAP), cellulose acetate trimellitate (CAT), hydroxypropyl methylcellulose phthalate, hydroxypropyl methylcellulose acetate, dioxypropyl methylcellulose succinate, carboxymethyl ethylcellulose (CMEC), hydroxypropyl methylcellulose acetate succinate (HPMCAS), and acrylic acid polymers and copolymers, typically formed from methyl acrylate, ethyl acrylate, methyl methacrylate and/or ethyl methacrylate with copolymers of acrylic and methacrylic acid esters (Eudragit NE, Eudragit RL, Eudragit RS). In one embodiment, the cysteamine product composition is administered in an oral delivery vehicle, including but not limited to, tablet or capsule form. Tablets are manufactured by first enterically coating the cysteamine product. A method for forming tablets herein is by direct compression of the powders containing the enterically coated cysteamine product, optionally in combination with diluents, binders, lubricants, disintegrants, colorants, stabilizers or the like. As an alternative to direct compression, compressed tablets can be prepared using wet-granulation or dry-granulation processes. Tablets may also be molded rather than compressed, starting with a moist material containing a suitable water-soluble lubricant.

The preparation of delayed, controlled or sustained/extended release forms of pharmaceutical compositions with the desired pharmacokinetic characteristics is known in the art and can be accomplished by a variety of methods. For example, oral controlled delivery systems include dissolution-controlled release (e.g., encapsulation dissolution control or matrix dissolution control), diffusion-controlled release (reservoir devices or matrix devices), ion exchange resins, osmotic controlled release or gastroretentive systems. Dissolution controlled release can be obtained, e.g., by slowing the dissolution rate of a drug in the gastrointestinal tract, incorporating the drug in an in soluble polymer, and coating drug particles or granules with polymeric materials of varying thickness. Diffusion controlled release can be obtained, e.g., by controlling diffusion through a polymeric membrane or a polymeric matrix. Osmotically controlled release can be obtained, e.g., by controlling solvent influx across a semipermeable membrane, which in turn carries the drug outside through a laser-drilled orifice. The osmotic and hydrostatic pressure differences on either side of the membrane govern fluid transport. Prolonged gastric retention may be achieved by, e.g., altering density of the formulations, bioadhesion to the stomach lining, or increasing floating time in the stomach. For further detail, see the Handbook of Pharmaceutical Controlled Release Technology, Wise, ed., Marcel Dekker, Inc., New York, N.Y. (2000), incorporated by reference herein in its entirety, e.g. Chapter 22 ("An Overview of Controlled Release Systems").

The concentration of cysteamine product in these formulations can vary widely, for example from less than about 0.5%, usually at or at least about 1% to as much as 15 or 20% by weight and are selected primarily based on fluid volumes, manufacturing characteristics, viscosities, etc., in accordance with the particular mode of administration selected. Actual methods for preparing administrable compositions are known or apparent to those skilled in the art and are described in more detail in, for example, Remington's Pharmaceutical Science, 15th ed., Mack Publishing Company, Easton, Pa. (1980).

Compositions useful for administration may be formulated with uptake or absorption enhancers to increase their efficacy. Such enhancers include, for example, salicylate, glycocholate/linoleate, glycholate, aprotinin, bacitracin, SDS, caprate and the like. See, e.g., Fix (J. Pharm. Sci., 85:1282-1285, 1996) and Oliyai and Stella (Ann. Rev. Pharmacol. Toxicol., 32:521-544, 1993).

The enterically coated cysteamine product can comprise various excipients, as is well known in the pharmaceutical art, provided such excipients do not exhibit a destabilizing effect on any components in the composition. Thus, excipients such as binders, bulking agents, diluents, disintegrants, lubricants, fillers, carriers, and the like can be combined with the cysteamine product. Oral delivery vehicles contemplated for use herein include tablets, capsules, comprising the product. For solid compositions, diluents are typically necessary to increase the bulk of a tablet or capsule so that a practical size is provided for compression. Suitable diluents include dicalcium phosphate, calcium sulfate, lactose, cellulose, kaolin, mannitol, sodium chloride, dry starch and powdered sugar. Binders are used to impart cohesive qualities to a oral delivery vehicle formulation, and thus ensure that a tablet remains intact after compression. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, hydroxyethyl cellulose, hypromellose, and the like), and Veegum. Lubricants are used to facilitate oral delivery vehicle manufacture; examples of suitable lubricants include, for example, magnesium stearate, calcium stearate, and stearic acid, and are typically present at no more than approximately 1 weight percent relative to tablet weight. Disintegrants are used to facilitate oral delivery vehicle, (e.g., a tablet) disintegration or "breakup" after administration, and are generally starches, clays, celluloses, algins, gums or crosslinked polymers. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. If desired, flavoring, coloring and/or sweetening agents may be added as well. Other optional components for incorporation into an oral formulation herein include, but are not limited to, preservatives, suspending agents, thickening agents, and the like. Fillers include, for example, insoluble materials such as silicon dioxide, titanium oxide, alumina, talc, kaolin, powdered cellulose, microcrystalline cellulose, and the like, as well as soluble materials such as mannitol, urea, sucrose, lactose, dextrose, sodium chloride, sorbitol, and the like.

A pharmaceutical composition may also comprise a stabilizing agent such as hydroxypropyl methylcellulose or polyvinylpyrrolidone, as disclosed in U.S. Pat. No. 4,301,146. Other stabilizing agents include, but are not limited to, cellulosic polymers such as hydroxypropyl cellulose, hydroxyethyl cellulose, methyl cellulose, ethyl cellulose, cellulose acetate, cellulose acetate phthalate, cellulose acetate trimellitate, hydroxypropyl methylcellulose phthalate, microcrystalline cellulose and carboxymethylcellulose sodium; and vinyl polymers and copolymers such as polyvinyl acetate, polyvinylacetate phthalate, vinylacetate crotonic acid copolymer, and ethylene-vinyl acetate copolymers. The stabilizing agent is present in an amount effective to provide the desired stabilizing effect; generally, this means that the ratio of cysteamine product to the stabilizing agent is at least about 1:500 w/w, more commonly about 1:99 w/w.

The tablet, capsule, or other oral delivery system is manufactured by first enterically coating the cysteamine product. A method for forming tablets herein is by direct compression of the powders containing the enterically coated cysteamine product, optionally in combination with diluents, binders, lubricants, disintegrants, colorants, stabilizers or the like. As an alternative to direct compression, compressed tablets can be prepared using wet-granulation or dry-granulation processes. Tablets may also be molded rather than compressed, starting with a moist material containing a suitable water-soluble lubricant.

In various embodiments, the enterically coated cysteamine product is granulated and the granulation is compressed into a tablet or filled into a capsule. Capsule materials may be either hard or soft, and are typically sealed, such as with gelatin bands or the like. Tablets and capsules for oral use will generally include one or more commonly used excipients as discussed herein.

In a further embodiment, the cysteamine product is formulated as a capsule. In one embodiment, the capsule comprises the cysteamine product and the capsule is then enterically coated. Capsule formulations are prepared using techniques known in the art.

A suitable pH-sensitive polymer is one which will dissolve in intestinal environment at a higher pH level (pH greater than 4.5), such as within the small intestine and therefore permit release of the pharmacologically active substance in the regions of the small intestine and not in the upper portion of the GI tract, such as the stomach.

For administration of the dosage form, i.e., the tablet or capsule comprising the enterically coated cysteamine product, a total weight in the range of approximately 100 mg to 1000 mg is used. The dosage form is orally administered to a subject need thereof.

In addition, various prodrugs can be "activated" by use of the enterically coated cysteamine Prodrugs are pharmacologically inert, they themselves do not work in the body, but once they have been absorbed, the prodrug decomposes. The prodrug approach has been used successfully in a number of therapeutic areas including antibiotics, antihistamines and ulcer treatments. The advantage of using prodrugs is that the active agent is chemically camouflaged and no active agent is released until the drug has passed out of the gut and into the cells of the body. For example, a number of produgs use S—S bonds. Weak reducing agents, such as cysteamine, reduce these bonds and release the drug. Accordingly, the compositions of the disclosure are useful in combination with pro-drugs for timed release of the drug. In this aspect, a pro-drug can be administered followed by administration of an enterically coated cysteamine compositions of the disclosure (at a desired time) to activate the pro-drug.

Dosing and Administration

The cysteamine product is administered in a therapeutically effective amount; typically, the composition is in unit dosage form. The amount of cysteamine product administered is, of course, dependent on the age, weight, and general condition of the patient, the severity of the condition being treated, and the judgment of the prescribing-physician. Suitable therapeutic amounts will be known to those skilled in the art and/or are described in the pertinent reference texts and literature. Current non-enterically coated doses are about 1.35 g/m$^2$ body surface area and are administered 4-5 times per day (Levtchenko et al., Pediatr Nephrol. 21:110-113, 2006). In one aspect, the dose is administered either one time per day or multiple times per day. The cysteamine product may be administered less than four time per day, e.g., one, two or three times per day. In some embodiments, an effective dosage of cysteamine product may be within the range of 0.01 mg to 1000 mg per kg (mg/kg) of body weight per day. In some embodiments, the cysteamine, cystamine or pharmaceutically acceptable salt thereof is administered at a daily dose ranging from about 10 mg/kg to about 250 mg/kg, or from about 100 mg/kg to about 250 mg/kg, or from about 60 mg/kg to about 100 mg/kg or from about 50 mg/kg to about 90 mg/kg, or from about 30 mg/kg to about 80 mg/kg, or from about 20 mg/kg to about 60 mg/kg, or from about 10 mg/kg to about 50 mg/kg. Further, the effective dose may be 0.5 mg/kg, 1 mg/kg, 5 mg/kg, 10 mg/kg, 15 mg/kg, 20 mg/kg/25 mg/kg, 30 mg/kg, 35 mg/kg, 40 mg/kg, 45 mg/kg, 50 mg/kg, 55 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, 250 mg/kg, 300 mg/kg, 350 mg/kg, 400 mg/kg, 450 mg/kg, 500 mg/kg, and may increase by 25 mg/kg increments up to 1000 mg/kg, or may range between any two of the foregoing values. In some embodiments, the cysteamine product is administered at a total daily dose of from approximately 0.25 g/m$^2$ to 4.0 g/m$^2$ body surface area, e.g., at least about 0.3, 0.4, 0.5, 0.6, 0.7, 0.8, 0.9, 1.0, 1.1, 1.2, 1.3, 1.4, 1.5, 1.6, 1.7, 1.8, 1.9 or 2 g/m$^2$, or up to about 0.8, 0.9, 1.0, 1.1, 1.2, 1.3, 1.4, 1.5, 1.6, 1.7, 1.8, 1.9, 2.0, 2.2, 2.5, 2.7, 3.0, 3.25, 3.5 or 3.75 g/m$^2$ or may range between any two of the foregoing values. In some embodiments, the cysteamine product may be administered at a total daily dose of about 0.5-2.0 g/m$^2$ body surface area, or 1-1.5 g/m$^2$ body surface area, or 1-1.95 g/m$^2$ body surface area, or 0.5-1 g/m$^2$ body surface area, or about 0.7-0.8 g/m$^2$ body surface area, or about 1.35 g/m$^2$ body surface area, or about 1.3 to about 1.95 grams/m2/day, or about 0.5 to about 1.5 grams/m2/day, or about 0.5 to about 1.0 grams/m2/day, preferably at a frequency of fewer than four times per day, e.g. three, two or one times per day. Salts or esters of the same active ingredient may vary in molecular weight depending on the type and weight of the salt or ester moiety. For administration of enteric dosage form, e.g., a tablet or capsule or other oral dosage form comprising the enterically coated cysteamine product, a total weight in the range of approximately 100 mg to 1000 mg is used.

Administration may continue for at least 3 months, 6 months, 9 months, 1 year, 2 years, or more.

Combination Therapy

Therapeutic compositions can be administered in therapeutically effective dosages alone or in combination with adjunct cancer therapy such as surgery, chemotherapy, radiotherapy, thermotherapy, and laser therapy, and may provide a beneficial effect, e.g. reducing tumor size, slowing rate of tumor growth, inhibiting metastasis, or otherwise improving overall clinical condition, without necessarily eradicating the cancer. Cytostatic and cytotoxic agents that target the cancer cells are specifically contemplated for combination therapy. Likewise, agents that target angiogenesis or lymphangiogenesis are specifically contemplated for combination therapy.

As used herein, a "chemotherapeutic agent" is a chemical compound useful in the treatment of cancer. Examples of chemotherapeutic agents include: alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and tiimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; vinca alkaloids; epipodophyllotoxins; antibiotics such as the enediyne antibiotics (e.g., calicheamicin, especially calicheamicin gammall and calicheamicin omegall; L-asparaginase; anthracenedione substituted urea; methyl hydrazine derivatives; dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; eflornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitiaerine; pentostatin; phenamet; pirarubicin; losoxantione; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2 2"-trichlorotiiethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® docetaxel (Rhône-Poulenc Rorer, Antony, France); chloranbucil; GEMZAR® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DFMO); retinoids such as retinoic acid; capecitabine; leucovorin (LV); irenotecan; adrenocortical suppressant; adrenocorticosteroids; progestins; estrogens; androgens; gonadotropin-releasing hormone analogs; and pharmaceutically acceptable salts, acids or derivatives of any of the above. Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON-toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASL® exemestane, formestanie, fadrozole, RIVISOR® vorozole, FEMARA® letrozole, and ARTMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF-A expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rJL-2; LURTOTECAN topoisomerase 1 inhibitor; ABARELLX® rmRH; and pharmaceutically acceptable salts, acids or derivatives of any of the above.

A "growth inhibitory agent" as used herein refers to a compound or composition which inhibits growth of a cell in vitro and/or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C.

Cytokines that are effective in inhibiting tumor metastasis are also contemplated for use in the combination therapy. Such cytokines, lymphokines, or other hematopoietic factors include, but are not limited to, M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IFN, TNFα, TNF1, TNF2, G-CSF, Meg-CSF, GM-CSF, thrombopoietin, stem cell factor, and erythropoietin.

In some embodiments, the methods described herein further comprise administering an MMP inhibitor (e.g., a MMP-2 inhibitor, a MMP-12 inhibitor and/or a MMP-9 inhibitor) to the subject. As used herein, "MMP inhibitor" is an agent that directly or indirectly inhibits MMP activity. This includes an agent that blocks MMP activity or an agent that blocks a pathway of MMP production. The agent causes a reduction in MMP activity in a cancer cell (or cancerous tissue) regardless of the mechanism of its action. Representative examples of MMP inhibitors include Tissue Inhibitors of Metalloproteinases (TIMPs) (e.g., TIMP-1, TIMP-2, TIMP-3, or TIMP-4), 02-macroglobulin, tetracyclines (e.g., tetracycline, minocycline, and doxycycline), hydroxamates (e.g., BATIMASTAT, MARIMISTAT and TROCADE), chelators (e.g., EDTA, cysteine, acetylcysteine, D-penicillamine, and gold salts), synthetic MMP fragments, succinyl mercaptopurines, phosphonamidates, and hydroxaminic acids.

Broad-spectrum inhibitors that inhibit more than one type of MMP are also contemplated. Exemplary broad spectrum MMP inhibitors include, but are not limited to, GM6001, batimastat, marimastat, prinomastat, BAY 12-9566, MMI270(B), BMS-275291, and metastat. Inhibitors that are capable of inhibiting MMP2, MMP9 or both MMP2 and MMP9 are specifically contemplated. An exemplary MMP-2/MMP-9 inhibitor includes, but is not limited to, SB-3CT. For example, in one embodiment, combination therapy comprising the administration of the cysteamine product and a MMP-2/MMP-9 inhibitor is specifically contemplated.

Assays for measuring MMP inhibition/suppression are readily known in the art, and include, for example, the following: Cawston T. E., Barrett A. J., "A rapid and reproducible assay for collagenase using (14C) acetylated collagen," Anal. Biochem. 35:1961-1965 (1963); Cawston T. E., Murphy G. "Mammalian collagenases," Methods in Enzymology 80:711 (1981); Koshy P. T. J., Rowan A. D., Life P. F., Cawston T. E., "96-well plate assays for measuring collagenase activity using (3)H-acetylated collagen," Anal. Biochem. 99:340-345 (1979); Stack M. S., Gray R. D., "Comparison of vertebrate collagenase and gelatinase using a new fluorogenic substrate peptide," J. Biol. Chem. 264: 4277-4281 (1989); and Knight C. G, Willenbrock F., Murphy G, "A novel coumarin-labelled peptide for sensitive continuous assays of the matrix metalloproteinases," FEBS Lett 296:263-266 (1992).

The treatment methods described herein optionally include monitoring the effect of the therapeutic composition on the tumor. For example, the size of the tumor can be determined, as can the presence of metastases. Also contemplated is measurement of the degree of metastasis, e.g., by measuring the number of metastatic modules or by measurement of ascites associated with metastasis.

The cysteamine product and other drugs/therapies can be administered in combination either simultaneously in a single composition or in separate compositions. Alternatively, the administration is sequential. Simultaneous administration is achieved by administering a single composition or pharmacological protein formulation that includes both the cysteamine product and other therapeutic agent(s). Alternatively, the other therapeutic agent(s) are taken separately at about the same time as a pharmacological formulation (e.g., tablet, injection or drink) of the cysteamine product.

In various alternatives, administration of the cysteamine product can precede or follow administration of the other therapeutic agent(s) by intervals ranging from minutes to hours. For example, in various embodiments, it is further contemplated that the agents are administered in a separate formulation and administered concurrently, with concurrently referring to agents given within 30 minutes of each other.

In embodiments where the other therapeutic agent(s) and the cysteamine product are administered separately, one would generally ensure that the cysteamine product and the other therapeutic agent(s) are administered within an appropriate time of one another so that both the cysteamine product and the other therapeutic agent(s) can exert, synergistically or additively, a beneficial effect on the patient. For example, in various embodiments the cysteamine product is administered within about 0.5-6 hours (before or after) of the other therapeutic agent(s). In various embodiments, the cysteamine product is administered within about 1 hour (before or after) of the other therapeutic agent(s).

In another aspect, the second agent is administered prior to administration of the cysteamine composition. Prior administration refers to administration of the second agent within the range of one week prior to treatment with cysteamine, up to 30 minutes before administration of cysteamine. It is further contemplated that the second agent is administered subsequent to administration of the cysteamine composition. Subsequent administration is meant to describe administration from 30 minutes after cysteamine treatment up to one week after cysteamine administration.

Animal Models

Cysteamine products can be evaluated in animal models known in the art for the disease indications contemplated herein. Exemplary animal models for metastatic cancers are described in Kim et al., (Biochem. Biophys. Res. Comm., 394:443-447, 2010) (breast cancer); Bresalier et al., (J. Clin. Invest., 87:1037-1045, 1991) (colorectal cancer); Furukawa et al., Cancer Res., 53:1204, 1993) (stomach cancer); Gingrich et al., (Cancer Res., 56:4096, 1996) (prostate cancer); Cranmer et al., (Melanoma Res., 15:325-356, 2005) (melanoma); Zheng et al., Oncogene, 26:6896-6904, 2007) (lung cancer); and Wang et al., (Neuropathol. Appl. Neurobiol., 37:189-205, 2011) (brain cancer).

Kits

The disclosure also provides kits for carrying out the methods of the disclosure. In various embodiments, the kit contains, e.g., bottles, vials, ampoules, tubes, cartridges and/or syringes that comprise a liquid (e.g., sterile injectable) formulation or a solid (e.g., lyophilized) formulation. The kits can also contain pharmaceutically acceptable vehicles or carriers (e.g., solvents, solutions and/or buffers) for reconstituting a solid (e.g., lyophilized) formulation into a solution or suspension for administration (e.g., by injection), including without limitation reconstituting a lyophilized formulation in a syringe for injection or for diluting concentrate to a lower concentration. Furthermore, extemporaneous injection solutions and suspensions can be prepared from, e.g., sterile powder, granules, or tablets comprising a cysteamine product-containing composition. The kits can also include dispensing devices, such as aerosol or injection dispensing devices, pen injectors, autoinjectors, needleless injectors, syringes, and/or needles. In various embodiments, the kit also provides an oral dosage form, e.g., a tablet or capsule or other oral formulation described herein, of the cysteamine product for use in the method. The kit also provides instructions for use.

While the disclosure has been described in conjunction with specific embodiments thereof, the foregoing description as well as the examples which follow are intended to illustrate and not limit the scope of the disclosure. Other aspects, advantages and modifications within the scope of the disclosure will be apparent to those skilled in the art.

EXAMPLES

Materials and Methods

Cell culture and reagents: Pancreatic cancer cell lines (HS766T, MIA-PaCa2, Panc-1, ASPC-1, PK-1, Mpanc96, BxPC-3, KLM, HPAF-II, and SW1990) were obtained from the American Type Culture Collection (Manassas, Va.). Cysteamine hydrochloride was purchased from Sigma-Aldrich (St. Louis, Mo.) and dissolved in distilled water.

Cell Migration Assay: Cell migration assay is a classical wound healing assay (25). For this assay, cells were cultured in 10 cm petri dishes until they were completely confluent. Cell monolayers were scraped with a sterile yellow micropipette tip and washed with PBS three times; the cells were then cultured in medium containing 0-5 mM of cysteamine for 24 hours. Five random fields were selected and pictures were taken using an inverted microscope. The average area (mm 2) of the gap between the cell layers was calculated using IPLab imaging software (BD Biosciences-Bioimaging, Rockville, Md.).

Matrigel invasion assay: Cell invasion was assayed in BD BioCoat Matrigel invasion chambers (BD Biosciences; 24 wells, 8 p.m pore size) as described previously (26). Briefly, cells were incubated with different concentrations of cysteamine (0-5 mM) for 24 hours. Non-invaded cells were removed from the upper surface of the membrane with a cotton swab, and cells on the lower surface of the membrane were fixed and stained with H&E. Three random fields per chamber were counted. Data were shown as mean±S.D. of triplicate determinations.

Cell viability assay: Cell viability of pancreatic cancer cell lines was measured by counting viable cell numbers. Briefly, $3 \times 10^5$ cells were seeded per well in a 6-well plate with 2.0 milliliter complete medium and incubated overnight for plating. The cells were treated with different concentrations of cysteamine for 24-48 hours. After incubation, cells were detached with trypsin, washed and stained with 0.4% trypan blue. Cell number was manually counted using a hemocytometer and presented as number of viable cells per milliliter.

Measurement of MMP activity: MMPs activity was measured by Mca-KPLGL-Dpa-AR-NH2 Fluorogenic Peptide Substrate (R&D systems, Emeryville, Calif.). Total cell protein from each pancreatic cancer cell line was collected using lysis buffer (containing 50 mM Tris-HCl, 10 mM $CaCl_2$, 0.05% Brij35 and 0.25% Triton-X) without an MMP inhibitor. Substrate and 10 µg of total cell protein in the buffer were mixed in a black-wall 96-well plate. After 1 hour incubation, fluorescence units were determined using excitation/emission=320/405 nm.

Substrate gel zymographic assay for MMP activity: Gelatin gel zyrnography was performed on cell lysates from H57666 and MIA-PaCa2 pancreatic cancer cell line with or without culture with different concentration of cysteamine essentially as previously described (27). Briefly, 50 µg of total protein was electrophoresed on 10% SDS-PAGE containing 0.1% gelatin as substrate. After washing with 1% Triton X-100 in 50 mM Tris/HCl, pH 7.5 for 1 hr to remove SDS, the gels were incubated overnight at 37° C. in 50 mM Tris/HCl, pH 7.5, containing 150 mM NaCl, 10 mM $CaCl_2$ and 0.1% Triton X-100, prior to staining with simply blue safe stain. The gels were washed with deionized water at room temperature. Gelatin-degrading enzymes were identified by their ability to digest gelatin as demonstrated by clear zones of digested gelatin. Relevant band intensities were quantified by scanning densitometric analysis and normalized to cell number.

Quantitative Reverse transcription-PCR (qRT-PCR): qRT-PCR was performed as described previously using QuantiTect SYBR Green PCR Kits (QIAGEN, Valencia, Calif.) (28). Gene specific primers for human MMP-9, MMP-12, MMP-14 and I3-actin were either purchased from QIAGEN or synthesized at the CBER core facility. Gene expression was normalized to β-actin before the fold change in gene expression was determined.

Enzyme-Linked ImmunoSorbent Assay (ELISA): The NIMP-9 protein level was determined using Human total MMP-9 DuoSet kit (R&D systems, Emeryville, Calif.) following the manufacturer's instruction. Ten microgram of total protein was aliquoted in each well and the MMP-9 concentration was determined by the colorimetric method.

$IC_{50}$ of cysteamine against MMPs activity: $IC_{50}$ of cysteamine and batimastat was determined using a fluorimetric MMP inhibitor profiling kit (Enzo Life Science, Farmingdale, N.Y.), following the manufacturer's instruction. Briefly, each MMP enzyme was mixed with various concentrations of cysteamine and batimastat in a black-wall 96 well plate and incubated for 30 minutes. After administration of fluorogenic substrate, a velocity of fluorescent increase was measured using excitation/emission=320/405 nm.

Measurement of metastasis, survival and body weight of animals implanted with orthotopic pancreatic cancer in mouse model: Female nude nu/nu mice between ages 5 and 6 weeks were maintained in a barrier facility in HEPA-filtered rack. All animal studies were conducted under approved protocol #2000-06 by the CBER Institutional Animal Care and Use Committee in accordance with the principles and procedures outlined in the NIH Guideline for the Care and Use of Laboratory Animals. For orthotopic tumor cell injection, the pancreas was carefully exposed, and $2.0 \times 10^6$ of MIA-PaCa2 and H5766T cells were injected into the organ. The pancreas was then returned to the peritoneal cavity, and the abdominal wall and skin were closed with skin clips (29, 30). From day 4 after tumor implantation, increasing doses of cysteamine (0, 25, 100, or 250 mg/kg/day) were subcutaneously injected twice a day until the end of the experiment. At day 30, mice were sacrificed and the number of metastatic nodules visible by naked eye and whose sizes were >5 mm in diameter counted. The total weight of primary tumor and metastatic nodules were also measured. Pictures were taken immediately after sacrificing the animals. Additionally, mouse survival time was monitored in an independent experiment. Mice were sacrificed when they had severe ascites or cachexia. Mice in both tumor models were weighed at day 10 and day 25 after Cysteamine treatment.

Measurement of enzymes in mouse serum: Mouse blood was collected from the tail vein. Serum levels of alanine aminotransferase (ALT), creatine kinase (CK), aldolase and creatinine (Cr) were measured using different kits obtained from Pointe Scientific, Inc. (Canton, Mich.) and Caldon Biotech, Inc. (Vista, Ca), following the manufacturer's instruction.

MMP activity and MMP-9 expression in primary tumors: When mice were sacrificed at day 30, primary tumors were collected. For extraction of total protein, the tumor was soaked with lysis buffer and homogenized using TissueRuptor (QIAGEN); the supernatant was collected. Total RNA was extracted using FastRNA pro green kit (MP Biomedicals, Solon, Ohio) following the manufacturer's instructions. MMP activity, gelatin hydrolyzing MMP activity and the mRNA and protein levels of MMP-9 were determined as mentioned above.

Statistical analysis: The data for enzymatic activity, ELISA, and qRT-PCR were compared between each group by ANOVA. Survival curves were generated by the Kaplan-Meier method and compared by using the log-rank test.

Example 1

Cysteamine Inhibits Pancreatic Cancer Cell Migration and Invasion without being Cytotoxic to Cells The following example describes the effect of cysteamine on pancreatic cancer cell invasion and migration.

The effect of cysteamine on pancreatic cancer cell invasion was determined using a matrigel invasion assay. For this assay, ten different pancreatic cancer cell lines in a matrigel invasion chamber were used. Results showed that cysteamine inhibited cell invasion in a concentration dependent manner Even the lowest concentration of cysteamine (0.05 mM) significantly inhibited cell invasion in all pancreatic cancer cell lines.

The effect of cysteamine on migration of the same pancreatic cancer cell lines in the invasion assay was also determined. For the migration assay, a wound healing assay was used (described above in Example 1). Results indicated that cell migration was significantly inhibited at and above 0.05 mM of cysteamine in all ten cell lines. Because cysteamine mediated similar effects in all ten cell lines used in these assays, two random cell lines were chosen for all other assays.

The cytotoxicity of cysteamine against two pancreatic cancer cell lines (H5766T and MIA-PaCa2) was also examined and the number of viable cells after 24 and 48 hour cysteamine treatment were counted. Cysteamine showed cell toxicity at >12.5 mM concentration in both cell lines tested but no evidence of toxicity was observed at lower concentrations as the number of viable cells was similar to untreated cells. These results suggest that both cell migration and invasion were inhibited at a noncytotoxic concentration of cysteamine.

Example 2

Cysteamine Inhibits MMP Enzymatic Activity in Pancreatic Cell Lines

The following Example investigated the mechanism of inhibition of cell migration and invasion by cysteamine, by evaluating the effect of cysteamine on MMP enzymatic activity.

Cysteamine inhibited MMP activity in two representative pancreatic cancer cell lines tested in a concentration-dependent manner. The $IC_{50}$ (the concentration of cysteamine at which 50% MMP enzyme activity (proteolysis) is inhibited) was calculated by ELISA (the results of which are provided below in Table 1).

TABLE 1

| MMP profiling. MMP profiling, $IC_{50}$ | | |
|---|---|---|
| | Cysteamine (μM) | Batimastat (nM) |
| MMP-1 | 290 | 13 |
| MMP-2 | 38 | 5.4 |
| MMP-3 | 330 | 300 |
| MMP-7 | 40 | 29 |
| MMP-8 | 240 | 9.8 |
| MMP-9 | 200 | 6.7 |
| MMP-10 | 310 | 52 |
| MMP-12 | 60 | 12 |
| MMP-13 | 460 | 6 |
| MMP-14 | 91 | 130 |

Cysteamine directly inhibited each MMP enzymatic activity, with an $IC_{50}$ of 38-460 μM. Since MMP-9 plays a central role in pancreatic cancer invasion, MMP-9 mRNA and protein levels were examined in both cell lines. In contrast to the enzymatic activity, protein and mRNA levels of MMP-9 were modestly increased at the highest concentration of cysteamine (5 mM). mRNAs for two other MMPs (i.e., MMP-12 and MMP-14) showed a modest increase similar to MMP-9 in response to cysteamine treatment. In contrast, zymographic gelatin hydrolyzing activity results for MMP-9 differed significantly from mRNA expression and both pro and active MMP-9 activities decreased significantly in a dose dependent manner.

Example 3

Cysteamine Decreases Metastasis and Prolongs Survival of Immunodeficient Mice Implanted Orthopically with Human Pancreatic Cancer The following example investigated the anti-metastasis effect of cysteamine in two orthotopic mouse models using human pancreatic cancer cell lines.

Figure 1A:
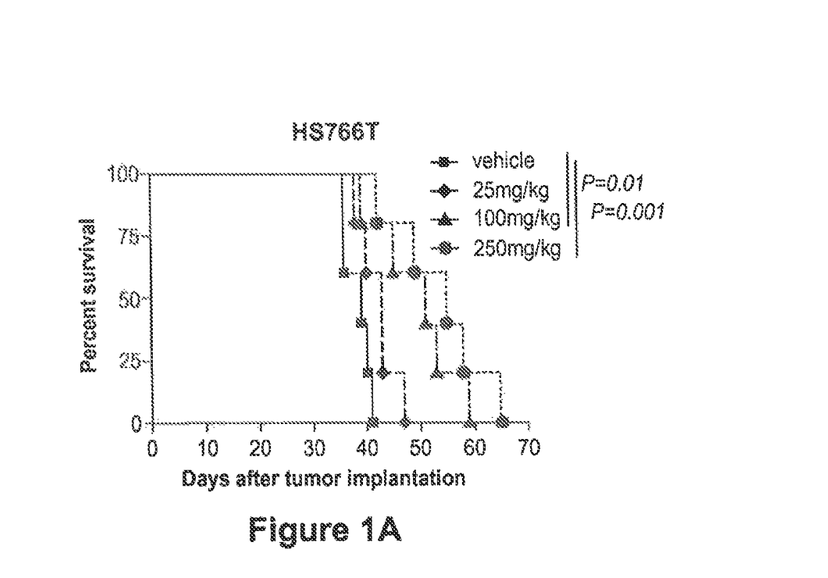
FIGS. 1A and 1B provide Kaplan-Meier survival curves of mice harboring HS766T (FIG. 1A) and MIA-PaCa2 (FIG. 1B) tumors.
Figure 1B:
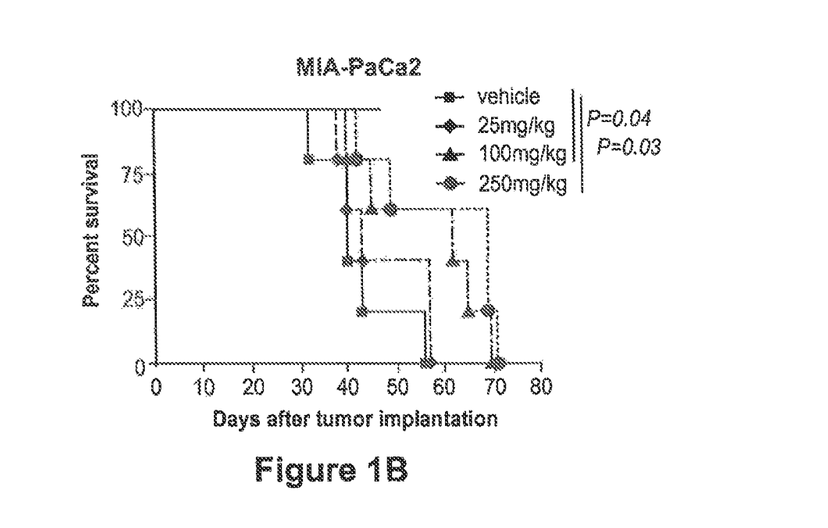

Mice were treated twice daily with cysteamine subcutaneously from day 4 after tumor implantation until the end of the experiment. At day 30, the number and weight of the primary tumor and metastatic nodules were measured. In both tumor models, the size and weight of the primary tumors did not show any difference between control and treated groups. However, cysteamine significantly decreased the number of metastatic nodules in a dose-dependent manner. At the highest dose (250 mg/kg/day), cysteamine significantly decreased the number of metastases of H5766T tumor by ~90% (from 34 to 3.6). The total weight of metastatic nodules of MIA-PaCa2 tumor was also decreased by ~90% at the highest dose. In addition, two of 5 mice in the H5766T tumor model and 4 of 5 mice in MIA-PaCa2 tumor model developed ascites in their peritoneal cavity. However, no mice developed ascites at 100 and 250 mg/kg/day dose in either tumor model. The survival of mice among different treatment groups was also determined. Mouse survival time was significantly prolonged when treated with 100 mg/kg/day cysteamine in both tumor models (FIGS. 1A and 1B).

The general condition and body weight of mice throughout the experimental period was also monitored. There was no significant difference in general appearance and body weight among four groups of animals in both tumor models. Similarly, there was no alteration in serum enzymes representing liver function (ALT) or muscle damage (Aldolase) nor evidence of skeletal muscle damage or kidney function (creatinine kinase and creatinine) in the cysteamine-treated groups. Moreover, no organ toxicity was detected in any vital organ such as the liver, kidney, brain, heart, and lung in cysteamine-treated mice when evaluated by histological examination.

Example 4

Cysteamine Decreases MMP Activity in Primary Orthotopic Tumors

MMP activity in primary orthotopic tumors was measured at day 30. Cysteamine decreased MMPs activity in both tumors (H5766T and MIA-PaCa2) at 100 and 250 mg/Kg cysteamine doses (FIG. 8A). In the same samples, mRNA was measured by q-RT-PCR and protein levels of MMP-9 by ELISA. In contrast to in vitro results, cysteamine did not affect mRNA and protein levels of MMP-9 in primary tumors harvested from mice. However, zymography assay for MMP-9 showed a dose dependent decrease in gelatinase activity.

Discussion

These results demonstrate that cysteamine inhibits pancreatic cancer cell migration and invasion through direct inhibition of MMP enzymatic activity in vitro. This newly discovered property of cysteamine resulted in inhibition of metastasis of human pancreatic cancer cells orthotopically implanted onto pancreas of immunodeficient mice; the effect was cysteamine dose-dependent. Cysteamine decreased not only the number of metastasis in the peritoneal cavity, but also decreased the ascites generated by aggressive pancreatic tumor metastasis. In contrast, no significant change in the size or weight of the primary pancreatic tumor was observed. Consistent with this observation, cysteamine did not cause any effect on cell viability in pancreatic cancer lines up to a concentration which caused significant inhibition of cell migration and invasion. Mice treated with cysteamine survived longer compared to control mice treated with excipient. Both in vitro and in primary tumors in vivo, MMP enzymatic activity decreased with cysteamine treatment while their expression at mRNA and protein levels did not change Zymographic results confirming that cysteamine induced MVP inhibition in vitro and in vivo. These observations indicate that blocking of catalytic activities of MMPs by cysteamine plays a role in the inhibition of tumor metastasis in animal model of pancreatic cancer.

The anti-metastatic effects of cysteamine were mediated without any visible signs of toxicity. Mice treated with even the highest dose of cysteamine (250 mg/kg/day) displayed no adverse effects related to general appearance, body weight, muscle damage, serum enzymes and serum creatinine levels. In addition, major organs from treated animals showed no evidence of histological damage. These observations are consistent with the known safety profile of cysteamine in humans (2,3). Cysteamine caused only gastrointestinal symptoms in subjects, as it increased gastric acid production and decreased gastrointestinal motility (31). However, these effects were controlled by concomitant use of proton-pump inhibitor (32). It is noteworthy that cysteamine sufficiently inhibited cancer cell migration and invasion in vitro at 50 µM, a concentration that can be achieved in vivo. Oral administration of cysteamine (given every 6 hours at 60 to 90 mg/kg of body weight per day) can increase the cysteamine plasma level up to ~50 µM (3.33-35). In addition, 100 mg/kg/day s.c. injection of cysteamine in animals is similar to the dosage used for cystinosis, and this dose produced a significant decrease in tumor metastasis and prolongation of survival. It is contemplated that cysteamine may be safely administered in the clinic to control pancreatic cancer metastasis.

Both mRNA and protein levels for MMP-9 were modestly to moderately upregulated in vitro at the highest dose of cysteamine. Similarly, mRNA of MMP-12 and 14 were also modestly upregulated at the highest dose. This increase in MMP-9 was not observed in vivo, perhaps because the pancreatic cancer cells were incubated with cysteamine only for 24 hours, while in vivo tumors were exposed to cysteamine continuously for 27 days. Cysteamine levels in tumors in vivo were not measured because intracellular metabolic fate of cysteamine in vivo is complex and difficult to measure as it binds to free thiol, particularly the cysteines of cellular proteins. Instead, activity and cysteamine levels were extrapolated to the biological effects of cysteamine on MMP activities and tumor growth. Nevertheless, the increased MMP-9, MMP-12 and MMP-14 levels at the highest concentration in vitro may represent a temporary compensatory effect of cells due to a sudden decrease of MMP activity by cysteamine. In contrast, the catalytic activity of MMP-9 to hydrolyze gelatin in zymography assay did not show such upregulation after treatment with highest dose of cysteamine of pancreatic cancer cell lines in vitro as well as orthotopic tumors in vivo. In fact in zymography assay for MMP-9, cysteamine caused a dose dependent decrease in gelatinase activity. These results suggest that enzymatic inhibition of MMP-9 by cysteamine may be involved in decrease of invasion and metastasis of pancreatic cancer. MMP1, MMP2, MMP7, and MMP9 have also been shown to be expressed in pancreatic tumor (36,37), but the effect of cysteamine on protein and mRNA levels for all these MMPs was not examined herein. However, it is important to point out that cysteamine inhibited enzymatic activity of MMPs, which includes all MMPs.

The anti-MMP activity of cysteamine was lower than that of specific MMP inhibitors such as batimastat and marimastat ($IC_{50}$ nM to low μM compared to high μM range for cysteamine), but cysteamine may be better tolerated in vivo. In fact, batimastat had problems of poor oral bioavailability (24) and marimastat failed in the clinic as higher dosage produced high musculoskeletal toxicities and poor survival in patients with breast cancer metastasis (38). In the present study, mice tolerated up to 250 mg/kg/day cysteamine without any visible, biochemical or histological evidence of toxicity or muscular damage.

In previous cancer treatment studies, cysteamine was used because of its anti-oxidative and radio-protective effects (39). During these studies, it was observed that cysteamine also had anti-carcinogenic and anti-proliferative activities in a variety of cancers. It is reported herein and in Fujisawa et al (PlosOne, 7:e34437, 2012) that cysteamine exerts anti-MMP and anti-metastatic effects. However, in this study cysteamine did not affect the primary pancreatic tumor size. Based on these insights, it is proposed that cysteamine can be useful as mono-therapy prior to surgery to prevent metastasis, as an adjuvant, or as a component of combination therapy for advanced stage disease to prolong survival of patients with pancreatic cancer.

All publications and patents mentioned herein are hereby incorporated by reference in their entirety as if each individual publication or patent was specifically and individually indicated to be incorporated by reference. In case of conflict, the present application, including any definitions herein, will control.

REFERENCES

1. Markello T C, Bernardini I M, Gahl W A (1993) Improved renal function in children with cystinosis treated with cysteamine N Engl J Med 328: 1157-1162.
2. Kleta R, Gahl W A (2004) Pharmacological treatment of nephropathic cystinosis with cysteamine Expert Opin Pharmacother 5: 2255-2262.
3. Dohil R, Gangoiti J A, Cabrera B L, Fidler M, Schneider J A, et al. (2010) Long-term treatment of cystinosis in children with twice-daily cysteamine J Pediatr 156: 823-827.
4. Besouw M, Levtchenko E (2011) Pharmacokinetics of cysteamine in a cystinosis patient treated with hemodialysis. Pediatr Nephrol 26: 639-640.
5. Gangoiti J A, Fidler M, Cabrera B L, Schneider J A, Barshop B A, et al. (2010) Pharmacokinetics of enteric-coated cysteamine bitartrate in healthy adults: a pilot study. Br J Clin Pharmacol 70: 376-382.
6. Watanabe H, Kamikawa M, Nakagawa Y, Takahashi T, Ito A (1988) The effects of ranitidine and cysteamine on intestinal metaplasia induced by X-irradiation in rats. Acta Pathol Jpn 38: 1285-1296.
7. Inano H, Onoda M, Suzuki K, Kobayashi H, Wakabayashi K (2000) Inhibitory effects of WR-2721 and cysteamine on tumor initiation in mammary glands of pregnant rats by radiation. Radiat Res 153: 68-74.
8. Tatsuta M, Iishi H, Yamamura H, Baba M, Mikuni T, et al. (1988) Inhibitory effect of prolonged administration of cysteamine on experimental carcinogenesis in rat stomach induced by N-methyl-N'-nitro-N-nitrosoguanidine. Int J Cancer 41: 423-426.
9. Jeitner T M, Renton F J (1996) Inhibition of the proliferation of human neural neoplastic cell lines by cysteamine Cancer Lett 103: 85-90.
10. Wu C, Shi L, Li Q, Jiang H, Selke M, et al. (2011) New strategy of efficient inhibition of cancer cells by carborane carboxylic acid-CdTe nanocomposites. Nanomedicine: Nanotechnology, Biology and Medicine.
11. Unak G, Ozkaya F, Medine E I, Kozgus O, Sakarya S, et al. (2012) Gold nanoparticle probes: design and in vitro applications in cancer cell culture. Colloids Surf B Biointerfaces 90: 217-226.
12. Yamada I, Seki S, Ito S, Suzuki S, Matsubara O, et al. (1991) The killing effect of 4-S-cysteaminylphenol, a newly synthesised melanin precursor, on B16 melanoma cell lines. Br J Cancer 63: 187-190.
13. Wan X M (2011) Autophagy-mediated chemosensitization by cysteamine in cancer cells. International Journal of Cancer 129: 1087-1095.
14. Jeitner T M, Oliver J R (1990) Possible oncostatic action of cysteamine on the pituitary glands of oestrogen-primed hyperprolactinaemic rats. J Endocrinol 127: 119-127.
15. Bramhall S R (1998) Stromal degradation by the malignant epithelium in pancreatic cancer and the therapeutic potential of proteolytic inhibition. J Hepatobiliary Pancreat Surg 5: 392-401.
16. Mollenhauer J, Roether I, Kern H F (1987) Distribution of extracellular matrix proteins in pancreatic ductal adenocarcinoma and its influence on tumor cell proliferation in vitro. Pancreas 2: 14-24.
17. Chang C, Werb Z (2001) The many faces of metalloproteases: cell growth, invasion, angiogenesis and metastasis. Trends Cell Biol 11: S37-43.
18. Basset P, Okada A, Chenard M P, Kannan R, Stoll I, et al. (1997) Matrix metalloproteinases as stromal effectors of human carcinoma progression: therapeutic implications. Matrix Biol 15: 535-541. d
19. Kilian M, Gregor J I, Heukamp I, Hanel M, Ahlgrimm M, et al. (2006) Matrix metalloproteinase inhibitor RO 28-2653 decreases liver metastasis by reduction of MMP-2 and MMP-9 concentration in BOP-induced ductal pancreatic cancer in Syrian Hamsters: inhibition of matrix metalloproteinases in pancreatic cancer. Prostaglandins Leukot Essent Fatty Acids 75: 429-434.
20. Anderson I C, Shipp M A, Docherty A J P, Teicher B A (1996) Combination Therapy Including a Gelatinase Inhibitor and Cytotoxic Agent Reduces Local Invasion and Metastasis of Murine Lewis Lung Carcinoma. Cancer Research 56: 715-718.
21. Eccles S A, Box G M, Court W J, Bone E A, Thomas W, et al. (1996) Control of lymphatic and hematogenous metastasis of a rat mammary carcinoma by the matrix metalloproteinase inhibitor batimastat (BB-94). Cancer Res 56: 2815-2822.
22. Shinoda K, Shibuya M, Hibino S, Ono Y, Matsuda K, et al. (2003) A novel matrix metalloproteinase inhibitor, FYK-1388 suppresses tumor growth, metastasis and angiogenesis by human fibrosarcoma cell line. Int J Oncol 22: 281-288.

23. Steward W P (1999) Marimastat (BB2516): current status of development. Cancer Chemother Pharmacol 43 Suppl. pp. S56-60.
24. Brown P D (2000) Ongoing trials with matrix metalloproteinase inhibitors. Expert Opin Investig Drugs 9: 2167-2177.
25. Wang H C, Wu D H, Chang Y C, Li Y J, Wang C J (2010) *Solanum nigrum* Linn. water extract inhibits metastasis in mouse melanoma cells in vitro and in vivo. J Agric Food Chem 58: 11913-11923.
26. Fujisawa T, Joshi B, Nakajima A, Puri R K (2009) A novel role of interleukin-13 receptor alpha2 in pancreatic cancer invasion and metastasis. Cancer Res 69: 8678-8685.
27. D'Angelo M, Billings P C, Pacifici M, Leboy P S, Kirsch T (2001) Authentic matrix vesicles contain active metalloproteases (MMP). a role for matrix vesicle-associated MMP-13 in activation of transforming growth factor-beta. J Biol Chem 276: 11347-11353.
28. Nakashima H, Fujisawa T, Husain S R, Puri R K (2010) Interleukin-13 receptor alpha2 DNA prime boost vaccine induces tumor immunity in murine tumor models. J Transl Med 8: 116.
29. Fujisawa T, Nakashima H, Nakajima A, Joshi B H, Puri R K (2011) Targeting IL-13R2 in human pancreatic ductal adenocarcinoma with combination therapy of IL-13-PE and gemcitabine. International Journal of Cancer 128: 1221-1231.
30. Shimamura T, Fujisawa T, Husain S R, Joshi B, Puri R K (2010) Interleukin 13 mediates signal transduction through interleukin 13 receptor alpha2 in pancreatic ductal adenocarcinoma: role of IL-13 *Pseudomonas* exotoxin in pancreatic cancer therapy. Clin Cancer Res 16: 577-586.
31. Wenner W J, Murphy J L (1997) The effects of cysteamine on the upper gastrointestinal tract of children with cystinosis. Pediatr Nephrol 11: 600-603.
32. Dohil R, Newbury R O, Sellers Z M, Deutsch R, Schneider J A (2003) The evaluation and treatment of gastrointestinal disease in children with cystinosis receiving cysteamine J Pediatr 143: 224-230.
33. Smolin L A, Clark K F, Thoene J G, Gahl W A, Schneider J A (1988) A comparison of the effectiveness of cysteamine and phosphocysteamine in elevating plasma cysteamine concentration and decreasing leukocyte free cystine in nephropathic cystinosis. Pediatr Res 23: 616-620.
34. Jonas A J, Schneider J A (1982) Plasma cysteamine concentrations in children treated for cystinosis. J Pediatr 100: 321-323.
35. Dohil R, Fidler M, Barshop B A, Gangoiti J, Deutsch R, et al. (2006) Understanding intestinal cysteamine bitartrate absorption. J Pediatr 148: 764-769.
36. Tamahashi U, Kumagai J, Takizawa T, Sekine M, Eishi Y (2008) Expression and intracellular localization of matrix metalloproteinases in intraductal papillary mucinous neoplasms of the pancreas. Virchows Arch 453: 79-87.
37. Schmalfeldt B, Prechtel D, Harting K, Spathe K, Rutke S, et al. (2001) Increased expression of matrix metalloproteinases (MMP)-2, MMP-9, and the urokinase-type plasminogen activator is associated with progression from benign to advanced ovarian cancer. Clin Cancer Res 7: 2396-2404.
38. Sparano J A, Bernardo P, Stephenson P, Gradishar W J, Ingle J N, et al. (2004) Randomized phase III trial of marimastat versus placebo in patients with metastatic breast cancer who have responding or stable disease after first-line chemotherapy: Eastern Cooperative Oncology Group trial E2196. J Clin Oncol 22: 4683-4690.
39. Apffel C A, Walker J E, Issarescu S (1975) Tumor rejection in experimental animals treated with radioprotective thiols. Cancer Res 35: 429-437.

What is claimed:

1. A method of treating malignant glioma comprising administering to a human subject with glioma, cysteamine, cystamine or a pharmaceutically acceptable salt thereof in an effective amount to inhibit or suppress metastasis of the malignant glioma, wherein the effective amount is less than an amount cytotoxic to the malignant glioma.

2. The method of claim 1, wherein the cysteamine, cystamine or pharmaceutically acceptable salt thereof is administered orally or parenterally.

3. The method of claim 1, wherein the cysteamine, cystamine or pharmaceutically acceptable salt thereof is administered up to four times a day.

4. The method of claim 1, wherein the administering results in increased thiol levels before administration of the cysteamine, cystamine or pharmaceutically acceptable salt thereof.

5. The method of claim 4, wherein the cysteamine, cystamine or pharmaceutically acceptable salt thereof is formulated in a tablet or capsule which is enterically coated.

6. The method of claim 4, further comprising administering an adjunct cancer therapy to the human subject with glioma.

7. The method of claim 6, wherein the adjunct cancer therapy is selected from the group consisting of chemotherapy, surgery, radiotherapy, thermotherapy, cancer vaccination, immunotherapy, gene therapy and laser therapy.

8. The method of claim 1, further comprising administering a further therapeutic agent selected from the group consisting of a matrix metalloproteinase (MMP) inhibitor, a chemotherapeutic agent, a growth inhibitory agent, a cancer vaccine, a gene therapy product, an immunotherapy and a cytokine.

9. The method of claim 1, wherein the cysteamine modulates enzymatic activity of at least one matrix metalloproteinase (MMP) selected from the group consisting of MMP-1, MMP-2, MMP-3, MMP-4, MMP-5, MMP-6, MMP-7, MMP-8, MMP-9, MMP-10, MMP-11, MMP-12, MMP-13, and MMP-14.

10. The method of claim 9, wherein the cysteamine decreases the enzymatic activity of the MMP in a primary tumor.

11. The method of claim 1, wherein the cysteamine, cystamine or pharmaceutically acceptable salt thereof is administered at a daily dose of from 10 mg/kg to 250 mg/kg.

12. The method of claim 1, wherein the cysteamine or pharmaceutically acceptable salt thereof is conjugated with nanoparticles.

13. A method of decreasing matrix metalloproteinase (MMP) enzymatic activity comprising administering to a human subject with malignant glioma, cysteamine, cystamine or a pharmaceutically acceptable salt thereof in an effective amount to decrease MMP enzymatic activity in the malignant glioma cell, the effective amount is less than an amount cytotoxic to the malignant glioma, and wherein the matrix metalloproteinase (MMP) is at least one selected from the group consisting of MMP-1, MMP-2, MMP-3, MMP-4, MMP-5, MMP-6, MMP-7, MMP-8, MMP-9, MMP-10, MMP-11, MMP-12, MMP-13, and MMP-14.

* * * * *